United States Patent [19]

Fugono et al.

[11] Patent Number: 5,738,993
[45] Date of Patent: Apr. 14, 1998

[54] OLIGONUCLEOTIDE AND METHOD FOR ANALYZING BASE SEQUENCE OF NUCLEIC ACID

[75] Inventors: Nobutake Fugono; Yasurou Kurusu; Masato Terasawa; Hideaki Yukawa, all of Ibaragi-ken, Japan

[73] Assignee: Mitsubishi Chemical Corporation, Japan

[21] Appl. No.: 662,963

[22] Filed: Jun. 13, 1996

Related U.S. Application Data

[63] Continuation of Ser. No. 392,147, Feb. 22, 1995, abandoned.

[30] Foreign Application Priority Data

Feb. 22, 1994 [JP] Japan .................................. 6-024168
Jun. 29, 1994 [JP] Japan .................................. 6-147291

[51] Int. Cl.$^6$ .......................... C12Q 1/68; C07H 19/00; C07H 21/04
[52] U.S. Cl. .......................... 435/6; 536/22.1; 536/24.3; 536/24.31
[58] Field of Search .......................... 435/6; 536/22.1, 536/24.3, 24.31

[56] References Cited

U.S. PATENT DOCUMENTS 4,775,619  10/1988  Urdea .................................. 435/6
5,187,085  2/1993  Lee .................................. 435/91.1

OTHER PUBLICATIONS

Brennan et al. (1986), "The effects of base analogue substitutions on the cleavage by the EcoRI restriction endonuclease of octadeoxyribonucleotides containing modified EcoRI recognition sequences", J. Biol. Chem. 261(16):7270–7278.

Ohtsuka et al. (1985), "An alternative approach to deoxyoligonucleotides as hybridization probes by insertion of deoxyinosine at ambiguous codon positions", J. Biol. Chem. 260(5):2605–2608.

Knoth et al. (1988), "Highly degenerate, inosine containing primer specifically amplify rare cDNA using the polymerase chain reaction", Nucleic Acids Res. 16(22):10932.

Stahl et al. (1978), "Transcription of T7 DNA containing modified nucleotides by bacteriophage T7 specific RNA polymerase", J. Biol. Chem. 253(14):4951–4959.

Martin et al. (1985), "Base pairing involving deoxyinosine:implications for probe design", Nucleic Acids Res. 13(24):8927–8938.

Dianov et al. (1991), "Preferential recognition of I–T basepairs in the initiation of excision repair by hypoxanthine–DNA glycosylase", Nucleic Acids Res. 19(14):3829–3833.

Lin et al. (1992), "Synthesis of oligodeoxyribonucleotides containing degenerate bases and their use as primers in the polymerase chain reaction", Nucleic Acids Res. 20(19) 5149–5152.

*Primary Examiner*—Ardin H. Marschel
*Assistant Examiner*—Jezia Riley
*Attorney, Agent, or Firm*—Wenderoth, Lind & Ponack

[57] ABSTRACT

An oligonucleotide comprising a specific region and one or two non-specific regions which are bound to at least one of the two termini of the specific region, wherein the specific region has a specific base sequence which is substantially complementary to a target sequence of a sample nucleic acid with which the oligonucleotide is to be hybridized, the non-specific region is composed of at least one nucleotide having other base capable of forming a base pair with each of bases constituting a common nucleic acid, or its oligomer, is used as a probe for the hybridization.

12 Claims, 1 Drawing Sheet

```
I I I I I I I I A G C T C A G T A C T G C A T G A T
| | | | | | | | : | | | | | | | | | | | | | | | | |
· · · · A G C T A G C T C C G A G T C A T G A C G T A C T A · · · ·
```

```
              A GCTCAGTACTGCATGAT
              : | | | | | | | | | | | | | | | | |
  ····AGCTAGCT C CGAGTCATGACGTACTA····
```

Fig. 1

```
  I I I I I I I I A GCTCAGTACTGCATGAT
  | | | | | | | | : | | | | | | | | | | | | | | | | |
  ····AGCTAGCT C CGAGTCATGACGTACTA····
```

Fig. 2

OLIGONUCLEOTIDE AND METHOD FOR ANALYZING BASE SEQUENCE OF NUCLEIC ACID

This application is a continuation of now abandoned application Ser. No. 08/392,147, filed Feb. 22, 1995.

TECHNICAL FIELD

The present invention relates to an oligonucleotide and a method for analyzing a base sequence of a nucleic acid. More specifically, the present invention relates to an oligonucleotide with a novel structure which can be preferably utilized as a probe for hybridization that is available for the determination of a base sequence of a nucleic acid, diagnosis of infectious diseases and hereditary diseases and analysis of a base sequence of a nucleic acid such as genome mapping, and to a method for analyzing a base sequence using the oligonucleotide.

BACKGROUND OF THE INVENTION

The analysis of the base sequence of the nucleic acid by hybridization has found widespread acceptance for, for example, the determination of the base sequence, the diagnosis of infectious diseases and hereditary diseases and for genome mapping. Sequencing by hybridization [SBH, R. Drmanac, et al., Science, 260, 1649 (1993)], which is a method for determining of the base sequence through hybridization has been expected to be put to practical use as a high-speed, less-costly method.

The analysis of the base sequence requires a technique of discriminating, among hybrids of a probe and a fragment of a target sequence which are formed by hybridization, a mismatched hybrid from a non-mismatched, completely complementary hybrid.

The hybridization reaction is an intricate reaction which is dominated by many factors such as the ionic strength of a reaction solution, the structure of the bases of a probe and sample DNA, the reaction temperature and reaction time. However, when a low molecular weight oligonucleotide is used as a probe, the mismatched hybrid is unstable in comparison to the completely complementary hybrid. Accordingly, it is considered logically possible to establish a system by which only the completely complementary hybrid can be detected by appropriately setting these conditions.

A method for chemically modifying bases of DNA for high-sensitivity hybridization [Proc. Natl. Acad. Sci., USA, 90, 11460 (1993)] and a method in which the washing after the hybridization is conducted at low temperatures for a long period time in order to enhance the ability of discriminating the mismatch [DNA and Cell Biology, 9, 527 (1990)] have been proposed so far, but this did not produce satisfactory results.

Especially, it is difficult to discriminate the hybridization in which a mismatch is present in the vicinity of a terminus of a probe from the hybridization free from a mismatch, with precision and at high sensitivity, which hinders the analysis of the base sequence from being put to practical use.

SUMMARY OF THE INVENTION

It is an object of this invention to provide an oligonucleotide which provides the results of the high-sensitivity hybridization to enhance the precision of the analysis of the base sequence of the nucleic acid by the hybridization and which can clearly discriminate a hybrid having a mismatched terminus from a completely complementary hybrid, as well as a method for analyzing a base sequence using the oligonucleotide.

The present inventors have conducted assiduous investigations to achieve the above-mentioned object, and have consequently found that when using an oligonucleotide in which a region composed of a certain nucleotide is bound to a terminus of a region having a specific base sequence to be hybridized with a fragment of a target sequence of a nucleic acid, the results of the high-sensitivity hybridization are obtained and the mismatch of the base pair can be detected at a high sensitivity. This finding has led to the completion of the present invention.

That is, the present invention provides an oligonucleotide comprising a specific region and one or two non-specific regions which are bound to at least one of two termini of the specific region, wherein the specific region has a specific base sequence which is substantially complementary to a target sequence of a sample nucleic acid with which the oligonucleotide is to be hybridized, the non-specific region is composed of at least one nucleotide having another base capable of forming a base pair with each of bases constituting a common nucleic acid, or its oligomer.

The present invention further provides a method for analyzing a base sequence of a nucleic acid, which comprises a step of hybridizing the above-mentioned oligonucleotide with a sample nucleic acid, and a step of discriminating the presence or absence of a target sequence complementary to the base sequence of the specific region of the above-mentioned oligonucleotide in the above-mentioned sample nucleic acid by the strength of hybridization or by the presence or absence of the hybridization.

In accordance with the present invention, the sensitivity of the hybridization can be increased, and the completely complementary hybrid can be easily discriminated from the mismatched hybrid, especially the mismatch at the terminus of the hybrid, which was difficult to be identified by the previous method, can be easily identified, thereby making it easy to analyze the DNA base sequence by means of hybridization.

BRIEF DESCRIPTION OF THE DRAWINGS

FIG. 1 is a schematic view showing a hybrid of a common oligonucleotide and a nucleic acid.

FIG. 2 is a schematic view showing a hybrid of an oligonucleotide of the present invention and a nucleic acid.

DETAILED DESCRIPTION OF THE INVENTION

The present invention will be described in more detail below.

The terms referred to in the present specification mean as follows.

The term "sample nucleic acid" means a nucleic acid which is to be hybridized with the oligonucleotide of the present invention for the analysis of the base sequence, and it may be either DNA or RNA. The term "specific region" means a region of which the base sequence is complementary to the target sequence of the sample nucleic acid which is capable of being hybridized and of which each base can be paired with the base of the target sequence. The term "bases constituting a common nucleic acid" means bases contained in a nucleotide constituting DNA or RNA, which include adenine (A), guanine (G), cytosine (C) and thymine (T) in DNA or A, G, C and uracil (U) in RNA. The term "base pair forming a specific pair" means a base pair between A and T or U, or a base pair between G and C.

The oligonucleotide of the present invention has the specific region and the one or two non-specific regions which are bound to at least one of both termini of the specific region. The oligonucleotide of the present invention may be either oligodeoxyribonucleotide or oligoribonucleotide.

The specific region has the specific base sequence which is substantially complementary to the target sequence of the sample nucleic acid. The term "substantially complementary" means the case that the base sequence is completely complementary to the target sequence and also the case that the base sequence has a mismatch of at least one base. The length of the specific region is not particularly limited so far as the specific region can act as a probe in the hybridization. The length of the specific region usually corresponds to from about 6 to 50 base pairs, preferably from about 6 to 20 base pairs. The base sequence of DNA in the hybridization region is not particularly limited either, and can be approximately determined depending on the base sequence of the sample DNA which base sequence is to be analyzed.

The non-specific region is composed of at least one nucleotide having other base which can form the base pair with the base constituting the common nucleic acid, or its oligomer. It is preferable that the above-mentioned base be bound equally to any base constituting the common nucleic acid. It is more preferable that the binding force be weaker than the binding force of the base pair that forms the specific pair.

A specific example of such a base is hypoxanthine. A specific example of the nucleotide is deoxyinosine which is deoxyribonucleotide having hypoxanthine as a base.

The number of nucleotides in the non-specific region or its oligomer is not particularly limited. It is usually at least 1, preferably from 2 to 20, more preferably from 2 to 8.

The position in which the non-specific region is bound to the specific region is not particularly limited either, and may be either the 5' terminus or the 3' terminus of the specific region. Further, the non-specific region may be bound to both the 5' terminus and the 3' terminus of the specific region. Of these cases, the latter is preferable.

The ratio of the length of the specific region and the length of the non-specific region varies depending on the length of the specific region and the GC content. It is preferable that the length of the specific region is the same or more than that of the non-specific region.

A method for synthesizing the oligonucleotide of the present invention is not particularly limited. Examples of the method include a method using β-cyanoethylphosphoamidite [Nucleic Acids Res. 12 4539 (1984)], a method using a phosphoric acid triester [Proc. Natl. Acad. Sci. USA 81 5956 (1984)], and a method using a phosphonic acid ester [Nucleic Acids Res. 14 5399 (1986)]. The binding of the specific region and the non-specific region may be conducted either after these regions are synthesized separately, or by adding the nucleotides of the non-specific region to the specific region one by one in order after the specific region is synthesized. Further, the specific region and the non-specific region may be synthesized simultaneously.

When the oligonucleotide of the present invention is used as a probe for the hybridization, the oligonucleotide may be used in the form immobilized on an insoluble carrier. Examples of the insoluble carrier include a filter made of nitrocellulose or nylon, a glass plate, porous glass, silica gel and latex. A method in which the oligonucleotide of the present invention is immobilized on the insoluble carrier is not particularly limited. For example, an amino-modified oligonucleotide is immobilized on a nylon filter having carboxyl groups in high-density on the surface via an amide bond by activating the carboxyl groups with water-soluble carbodiimide [J. Org. 26 2525 (1961)]. Further, a biotin-modified oligonucleotide is immobilized on a carrier having a surface coated with avidin by the biotin-avidin reaction [Biochemistry 11 2291 (1972)]. Still further, an amino-modified oligonucleotide is immobilized on silica gel having tolesyl groups introduced therein [Analytical Chemistry Symposium Series 9, 203 (1981)]. Moreover, examples of a method for producing an oligonucleotide immobilized on a filter include a method in which many kinds of DNA are synthesized simultaneously on a solid phase by a method using photolithography [Science, 251 767 (1991)], and a method in which reagents for synthesizing DNA are in contact with a sealed glass plate [Nucleic Acids Res. 22 1368 (1994)].

The above-mentioned oligonucleotide of the present invention can be utilized in the analysis of the base sequence of the nucleic acid. That is, the method for analyzing the base sequence of the nucleic acid in the present invention comprises a step of hybridizing the above-mentioned oligonucleotide with the sample nucleic acid, and a step of identifying the presence or absence of the target sequence which is complementary to the base sequence of the specific region of the oligonucleotide in the sample nucleic acid by the strength of hybridization or the presence or absence of the hybridization. In accordance with the method of the present invention, the sensitivity of the hybridization can be increased, and the completely complementary hybrid can be easily discriminated from the mismatched hybrid, and especially the hybrid having the mismatched terminus, which was difficult to be discriminated by the previous method, can be easily discriminated, whereby the base sequence of DNA can be easily analyzed by the hybridization.

Next, it is explained how the mismatched hybridization can be discriminated from the mismatch-free hybridization accurately at a high sensitivity in the hybridization using the oligonucleotide of the present invention. FIG. 1 is a schematic view showing a hybrid of a common oligonucleotide and a sample nucleic acid which is almost complementary to this oligonucleotide but mismatched. In general, when the mismatch is present in the center of the hybrid, it is a serious obstacle to the hybridization. However, the mismatch which is present near the terminus of the hybrid is not so serious as that in the center.

The hybrid of the oligonucleotide of the present invention which has the specific region of the same sequence as the above-mentioned oligonucleotide and the above-mentioned sample nucleic acid is schematically shown in FIG. 2. In FIG. 2, I is inosine. As shown in FIG. 2, inosine can form a base pair with any nucleotide. Therefore, the length of the hybrid can be extended by the length of the non-specific region. That is, the mismatch present at the terminus of the hybrid with the common oligonucleotide comes to be present in the center of the hybrid with the oligonucleotide of the present invention. Further, the strength of hybridization increases. Accordingly, the mismatch-free hybridization can be easily discriminated from the mismatched hybridization. If the non-specific region is bound to the 5' terminus of the specific region, the mismatch at the 5' terminus of the specific region can be easily detected. If the non-specific region is bound to the 3' terminus of the specific region, the mismatch at the 3' terminus of the specific region can be easily detected. Further, if the non-specific region is bound to both the 5' terminus and the 3' terminus of the specific region, both of the mismatches at the 5' terminus and the 3' terminus of the specific region can be easily detected.

The conditions for the hybridization using the oligonucleotide of the present invention are not particularly limited, and the optimum conditions can vary depending on the kind and the sequence of the sample nucleic acid and the sequence of the oligonucleotide. For example, when a relatively short-chain oligonucleotide is used, it is advisable that mild conditions be set, for instance, that the temperature of the hybridization be low. When a large amount of a GC residue is present in the DNA base sequence, the stability of the hybrid becomes higher than when a large amount of an AT residue is present therein. However, a method using a quaternary amine salt such as tetramethylammonium chloride [Proc. Natl. Acad. Sci. USA 82, 1585 (1985)] is effective for offsetting the above-mentioned phenomenon. Besides, a method in which a surface active agent such as sodium dodecylsulfate or sodium N-lauroylsarcosinate is added to a hybridization solution is also effective for improving the sensitivity of the hybridization (refer to Example C).

When the base sequence of the nucleic acid is analyzed by the hybridization, it is advisable that either the sample nucleic acid or the oligonucleotide of the present invention be labeled. The labeling method is not particularly limited. Examples of the labeling method include a method using a radioisotope and a method using a fluorescent pigment. The results of the hybridization can be measured by methods corresponding to the various labeling methods.

The method for analyzing the base sequence in the present invention can be applied for the determination of a DNA base sequence via hybridization [Genomics, 13 1378 (1922)], diagnosis of infectious diseases and hereditary diseases, and the mapping of giant genome DNA. In the diagnosis of the infectious diseases, for example, DNA is extracted from a blood of a test person, a DNA probe is prepared from sequences peculiar to various diseases with respect to the extracted DNA according to the method of the present invention, and the hybridization reaction is performed to detect the presence of diseases. In the diagnosis of hereditary diseases, the oligonucleotide is prepared on the basis of the sequence specific to the gene that causes the hereditary disease according to the method of the present invention, and hybridized with chromosome DNA obtained from a test person, and the presence or absence of the transversion of the gene is detected. The mapping of giant genome DNA is a technology which is essential for the project of analyzing genome DNA. The hybridization with many DNA probes prepared by the method of the present invention is conducted with respect to the genome bank, whereby the position of each clone on the genome can be determined [abstract of 16th Annual Meeting of Japan Molecular Biology Academy, 1334 (1993)]. The DNA base sequence is ordinarily determined by a method in which DNA is analyzed chemically [Proc. Natl. Acad. Sci. USA, 74 560 (1977)] or a method in which DNA is analyzed with a DNA synthetase. A method for analyzing a DNA base sequence via the hybridization (sequencing by hybridization: SBH) has attracted some attention recently. [Science, 260 1649 (1993)]. SBH is a technology in which a base sequence of intended long-chain DNA is determined by selectively hybridizing the intended long-chain DNA with only an oligo-DNA probe completely complementary to the DNA under suitable conditions for the hybridization, and collecting and analyzing the data of the specifically hybridized oligo-DNA probe.

Further, the oligonucleotide of the present invention is also expected to be used as a primer of a polymerase chain reaction (PCR) or a polymerase reaction in the determination of the base sequence.

DESCRIPTION OF PREFERRED EMBODIMENTS

The present invention will be illustrated more specifically by referring to the following Examples. However, the present invention is not limited at all to these Examples.

EXAMPLE A

Measurement of the Strength of Hybridization (A) Synthesis of an oligonucleotides:

Oligonucleotides of the present invention, oligonucleotides for comparative examples and a sample DNA having sequences shown in Table 1 were synthesized by means of a DNA synthesizer [394 DNA/RNA Synthesizer, a trade name for a device manufactured by Applied Biosystems (ABI)].

Oligonucleotide Nos. described below correspond to SEQ ID NO: in the Sequence Listing. In the sequences, "I" symbolizes deoxyinosine.

TABLE 1

| Oligonucleotide | Nucleotide Sequence | Remarks |
| --- | --- | --- |
| 1 Comparative Example 1 | 5'-XCCCCTTTT-3' | SEQ ID NO: 1 For Example 1 |
| 2 Comparative Example 2 | 5'-XTTCCCCTT-3' | SEQ ID NO: 2 For Example 2 |
| 3 Comparative Example 3 | 5'-XCCTTTTCC-3 | SEQ ID NO: 3 For Example 3 |
| 4 Comparative Example 4 | 5'-XCTCTCTCT-3' | SEQ ID NO: 4 For Example 4 |
| 5 Example 1 | 5'-XIIICCCCTTTT-3' | SEQ ID NO: 5 |
| 6 Example 2 | 5'-XIIITTCCCCTT-3' | SEQ ID NO: 6 |
| 7 Example 3 | 5'-XIIICCTTTTCC-3' | SEQ ID NO: 7 |
| 8 Example 4 | 5'-XIIICTCTCTCT-3' | SEQ ID NO: 8 |
| 9 Sample DNA | 5'-AGGAAAAGGGGAAGAGAGAGA-3' | SEQ ID NO: 9 for Oligonucleotide Nos. 1 to 8 |

TABLE 1-continued

| Oligonucleotide | Nucleotide Sequence | Remarks |
| --- | --- | --- |
| 10 Comparative Example 5 | 5'-XCCTTTTCC-3' | SEQ ID NO: 10 for Examples 5 to 8 |
| 11 Example 5 | 5'-XIIIICCTTTTCC-3' | SEQ ID NO: 11 |
| 12 Example 6 | 5'-XIIIICCTTTTCCIIII-3' | SEQ ID NO: 12 |
| 13 Example 7 | 5'-XIIIIIIICCTTTTCC-3' | SEQ ID NO: 13 |
| 14 Example 8 | 5'-XIIIIIIICCTTTTCCIIIIIII-3' | SEQ ID NO: 14 |
| 15 Sample DNA | 5'-AGAGAGAGAGGAAAAGGAGAGAGAGA-3' | SEQ ID NO: 15 for Oligonucleotide Nos. 10 to 14 |

In Table 1, X is Aminolink 2™, and I is deoxyinosine.

The above-mentioned oligonucleotide and the sample DNA were synthesized according to a standard protocol, and the synthesis was completed in a cycle in which the trityl group as a protective group of the 5' terminus was not removed. The sample DNA (9) in Table 1 was purified by means of an OPC cartridge (made by ABI). The oligonucleotides and the sample DNA (1) to (9) in Table 1 were concentrated to dryness. Then, the oligonucleotides (1) to (8) were suspended in a 0.5M sodium bicarbonate buffer solution (pH 8.4), and the sample DNA (9) was suspended in a TE buffer solution. The amount of each of (1) to (9) was adjusted to 1 nmol/μl upon measuring an absorbance of 260 nm.

(B) Immobilization of the oligonucleotide

The oligonucleotide was immobilized in the following manner by amide-bonding the amino groups of the amino-modified oligonucleotide to a nylon membrane having a high-density anionic carboxyl group on the surface.

A Biodine C (a trade name for a product made by Poll K.K.) membrane was washed with 0.1N HCl for acidification, and then dipped in 20% 1-ethyl-3-dimethylaminopropylcarbodiimide hydrochloride (EDC) at room temperature for from 15 to 30 minutes. The thus-obtained membrane was washed slightly with deionized water and with a 0.5M sodium bicarbonate buffer solution (pH 8.4), and then set at a dot blotting device (manufactured by Bio-Rad). The amino-modified oligonucleotide suspended in the 0.5M sodium bicarbonate buffer solution (pH 8.4) was reacted with the membrane at room temperature for 15 minutes. The membrane which was washed with a mixed solution of a tris-buffer solution (TBS) and 0.1% Tween-20 was treated with 0.1N NaOH for 10 minutes, washed slightly with deionized water and air-dried.

(C) Labeling of the sample DNA

The sample DNA was labeled as follows. That is, the 5' terminus of the sample DNA was radioactively labeled with [γ-$^{32}$P]ATP. The reaction was conducted by means of a DNA 5' terminus labeling kit (MEGALABEL™, a trade name for a product made by Takara Shuzo Co., Ltd.).

(D) Hybridization reaction

The above-mentioned filter on which the oligonucleotide was immobilized and the radioactively labeled sample DNA were hybridized in a buffer solution of 5× SSC (750 mM sodium chloride-75 mM trisodium citrate) and 0.1% SDS (sodium dodecylsulfate) at from 4° to 10° C. for from 1 hour to one night. After the completion of the hybridization, the hybrid was washed three times with a buffer solution of 2× SSC and 0.1% SDS at from 4° to 10° C. for 5 minutes, and air-dried. Subsequently, the radiation dose of each dot was measured by autoradiography to calculate the strength of the hybridization.

The results are shown in Table 2. In the Table 2, the strength of hybridization of the oligonucleotide in Comparative Examples was rated at 1, and that of the oligonucleotide in Examples was indicated on this basis. It was found that the amount of hybridization varies depending on the sequence of the specific region, but increases in any sequence by introducing inosine (non-specific region), and that with exactly the same kind and number of the binding, the introduction of inosines in both the 3' and 5' termini gives the higher strength of hybridization than the introduction of inosine in only the 5' terminus. The hybridization at the high sensitivity is realized by introducing inosines in both the 3' and 5' termini.

TABLE 2

| Oligonucleotide | Nucleotide Sequence | Strength of Hybridization | Remarks |
| --- | --- | --- | --- |
| 1 Comparative Example 1 | 5'-XCCCCTTTT-3' | 1.0 | SEQ ID NO: 1 |
| 5 Example 1 | 5'-XIIIICCCCTTTT-3' | 96 | SEQ ID NO: 5 |
| 2 Comparative Example 2 | 5'-XTTCCCCTT-3' | 1.0 | SEQ ID NO: 2 |
| 6 Example 2 | 5'-XIIIITTCCCCTT-3' | 29 | SEQ ID NO: 6 |
| 3 Comparative Example 1 | 5'-XCCTTTTCC-3' | 1.0 | SEQ ID NO: 3 |
| 7 Example 3 | 5'-XIIIICCTTTTCC-3' | 20 | SEQ ID NO: 7 |
| 4 Comparative Example 4 | 5'-XCTCTCTCT-3' | 1.0 | SEQ ID NO: 4 |
| 8 Example 4 | 5'-XIIIICTCTCTCT-3' | 18 | SEQ ID NO: 8 |
| 10 Comparative Example 5 | 5'-XCCTTTTCC-3' | 1.0 | SEQ ID NO: 10 |
| 11 Example 5 | 5'-XIIIICCTTTTCC-3' | 20 | SEQ ID NO: 11 |
| 12 Example 6 | 5'-XIIIICCTTTTCCIIII-3' | 51 | SEQ ID NO: 12 |
| 13 Example 7 | 5'-XIIIIIIICCTTTTCC-3' | 25 | SEQ ID NO: 13 |
| 14 Example 8 | 5'-XIIIIIIICCTTTTCCIIIIIII-3' | 72 | SEQ ID NO: 14 |

EXAMPLE B

Discrimination of Mismatch (A) Synthesis of oligonucleotides:

Oligonucleotides of the present invention, oligonucleotides for comparative examples and a sample DNA having sequences shown in Table 3 were synthesized by means of a DNA synthesizer (394 DNA/RNA Synthesizer, a trade name for a device manufactured by Applied Biosystems, ABI) in the same manner as in (A) of the above-mentioned Example A.

TABLE 3

| Oligonucleotide | Nucleotide Sequence | Remarks |
| --- | --- | --- |
| 16 Control 1 | 5'-XCCTTTTCC-3' | SEQ ID NO: 16 For Comparative Examples 6 to 8 |
| 17 Comparative Example 6 | 5'-XTCTTTTCC-3' | SEQ ID NO: 17 For Examples, 9, 12, 15 and 18 |
| 18 Comparative Example 7 | 5'-XCCTGTTCC-3' | SEQ ID NO: 18 For Examples 10, 13, 16 and 19 |
| 19 Comparative Example 8 | 5'-XCCTTTTCT-3' | SEQ ID NO: 19 For Examples 11, 14, 17 and 20 |
| 20 Control 2 | 5'-XIIIICCTTTTCC-3' | SEQ ID NO: 20 For Examples 9 to 11 |
| 21 Example 9 | 5'-XIIIITCTTTTCC-3' | SEQ ID NO: 21 |
| 22 Example 13 | 5'-XIIIICCTGTTCC-3' | SEQ ID NO: 22 |
| 23 Example 17 | 5'-XIIIICCTTTTCT-3' | SEQ ID NO: 23 |
| 24 Control 3 | 5'-XIIIICCTTTTCCIIII-3' | SEQ ID NO: 24 for Examples 12 to 14 |
| 25 Example 10 | 5'-XIIIITCTTTTCCIIII-3' | SEQ ID NO: 25 |
| 26 Example 14 | 5'-XIIIICCTGTTCCIIII-3' | SEQ ID NO: 26 |
| 27 Example 18 | 5'-XIIIICCTTTTCTIIII-3' | SEQ ID NO: 27 |
| 28 Control 4 | 5'-XIIIIIIIICCTTTTCC-3' | SEQ ID NO: 28 for Examples 15 to 17 |
| 29 Example 11 | 5'-XIIIIIIIITCTTTTCC-3' | SEQ ID NO: 29 |
| 30 Example 15 | 5'-XIIIIIIIICCTGTTCC-3' | SEQ ID NO: 30 |
| 31 Example 19 | 5'-XIIIIIIIICCTTTTCT-3' | SEQ ID NO: 31 |
| 32 Control 5 | 5'-XIIIIIIIICCTTTTCCIIIIIIII-3' | SEQ ID NO: 32 for Examples 18 to 20 |
| 33 Example 12 | 5'-XIIIIIIIITCTTTTCCIIIIIIII-3' | SEQ ID NO: 33 |
| 34 Example 16 | 5'-XIIIIIIIICCTGTTCCIIIIIIII-3' | SEQ ID NO: 34 |
| 35 Example 20 | 5'-XIIIIIIIICCTTTTCTIIIIIIII-3' | SEQ ID NO: 35 for Oligonucleotide Nos. 16 to 35 |
| 15 Sample DNA | 5'-AGAGAGAGAGGAAAAGGAGAGAGAGA-3' | SEQ ID NO: 15 |

In Table 3, X is aminolink 2, and I is inosine.

(B) Immobilization of the oligonucleotide

The oligonucleotide was immobilized in the same manner as in (B) of Example A.

(C) Labeling of the sample DNA

The sample DNA was labeled in the same manner as in (C) of Example A.

(D) Hybridization reaction

The hybridization was conducted in the same manner as in (D) of Example A.

(E) Calculation of the ability of identifying a mismatch

The ability to identify a mismatch was calculated from the results obtained by the hybridization. The ability to identify a mismatch is indicated on the basis of the following discrimination value (D value) as an index, showing easiness of discriminate a mismatch.

$$D \text{ value} = \frac{\text{Amount of hybridization of a sequence completely complementary to sample DNA}}{\text{Amount of hybridization of a mismatched sequence}}$$

The amount of hybridization of the sequence completely complementary to the sample DNA indicates an amount of hybridization of a sequence in Control. The amount of hybridization of the mismatched sequence indicates an amount of hybridization of a sequence in Comparative Example or Example corresponding to the sequence in Control. The D value is the ratio of the amount of hybridization of the sequence in Comparative Example or Example to the amount of hybridization of the sequence in Control. That is, the D value of the sequence in Control is rated at 1. If the D value is high in Comparative Example or Example, the sequence in Comparative Example or Example can be easily discriminated from the sequence in Control (amount of hybridization in Comparative Example or Example is small relative to that in the Control).

Table 4 shows the D value of each sequence. The oligonucleotide having inosine introduced therein has the high D value, and especially the oligonucleotide in which inosines are introduced in both the 3' and 5' termini has a higher D value. It has been found that the oligonucleotide having inosine introduced therein, especially the oligonucleotide in which inosines are introduced in both the 3' and 5' termini has excellent ability to identify a mismatch.

TABLE 4

Ability to identify a mismatch (D value)

| Oligonucleotide | Nucleotide Sequence | D value | Remarks |
| --- | --- | --- | --- |
| 17 Comparative Example 6 | 5'-XTCTTTTCC-3' | 3 to 5 | SEQ ID NO: 17 |
| 21 Example 9 | 5'-XIIIITCTTTTCC-3' | 26 | SEQ ID NO: 21 |
| 25 Example 10 | 5'-XIIIITCTTTTCCIIII-3' | 40 | SEQ ID NO: 25 |
| 29 Example 11 | 5'-XIIIIIIIITCTTTTCC-3' | 17 | SEQ ID NO: 29 |
| 33 Example 12 | 5'-XIIIIIIIITCTTTTCCIIIIIIII-3' | 31 | SEQ ID NO: 33 |
| 18 Comparative Example 7 | 5'-XCCTGTTCC-3' | 4 to 5 | SEQ ID NO: 18 |
| 22 Example 13 | 5'-XIIIICCTGTTCC-3' | more than 1000 | SEQ ID NO: 22 |
| 26 Example 14 | 5'-XIIIICCTGTTCCIIII-3' | 98 | SEQ ID NO: 26 |

TABLE 4-continued

Ability to identify a mismatch (D value)

| | Oligonucleotide | Nucleotide Sequence | D value | Remarks |
|---|---|---|---|---|
| 30 | Example 15 | 5'-XIIIIIIIICCTGTTCC-3' | more than 1000 | SEQ ID NO: 30 |
| 34 | Example 16 | 5'-XIIIIIIIICCTGTTCCIIIIIII-3' | 560 | SEQ ID NO: 34 |
| 19 | Comparative Example 8 | 5'-XCCTTTTCT-3' | 3 to 5 | SEQ ID NO: 19 |
| 23 | Example 17 | 5'-XIIIICCTTTTCT-3' | 14 | SEQ ID NO: 23 |
| 27 | Example 18 | 5'-XIIIICCTTTTCTIIII-3' | 26 | SEQ ID NO: 27 |
| 31 | Example 19 | 5'-XIIIIIIIICCTTTTCT-3' | 7 | SEQ ID NO: 31 |
| 27 | Example 20 | 5'-XIIIIIIIICCTTTTCTIIIIIII-3' | 24 | SEQ ID NO: 27 |

EXAMPLE C

Influence of a Surface Active Agent on a Hybridization Reaction (A) Synthesis of DNA Oligonucleotide of the present invention, an oligonucleotide for comparative examples and a sample DNA having sequences as shown in Table 5 were synthesized by means of a DNA synthesizer (394 DNA/RNA Synthesizer, a trade name for a device manufactured by Applied Biosystems, ABI) in the same manner as in (A) of the above-mentioned Example A.

TABLE 5

| Oligonucleotide | Nucleotide Sequence | Remarks |
|---|---|---|
| 16 | 5'-XCCTTTTCC-3' | SEQ ID NO: 16 For Control 1 and Example 1 |
| 24 | 5'-XIIIICCTTTTCCIIII-3' | SEQ ID NO: 24 For Control 2 and Example 2 |
| 15 | 5'-AGAGAGAGAGGAAAAGGAGAGAGAGA-3' | SEQ ID NO: 15 For Sample DNA |

In Table 5, X is Aminolink 2™, and I is inosine.

(B) Immobilization of the oligonucleotide

The oligonucleotide was immobilized in the same manner as in (B) of Example A.

(C) Labeling of the sample DNA

The sample DNA was labeled in the same manner as in (C) of Example A.

(D) Hybridization reaction

The above-mentioned filter on which the oligonucleotide was immobilized and the radioactively labeled sample DNA were hybridized in a buffer solution of 5× SSC (750 mM sodium chloride·75 mM trisodium citrate) and 7% sodium N-lauroylsarcosinate at from 4° to 10° C. for from 1 hour to one night. After the completion of the hybridization, the hybrid was washed three times with a buffer solution of 2× SSC and 0.1% SDS at from 4° to 10° C. for 5 minutes, and air-dried. Further, as a control experiment, the above-mentioned filter on which the oligonucleotide was immobilized was subjected to the hybridization in a buffer solution of 5× SSC (750 mM sodium chloride-75 mM trisodium citrate) at from 4° to 10° C. for from 1 hour to one night. After the completion of the hybridization, the hybrid was washed three times with a 2× SSC buffer solution at from 4° to 10° C. for 5 minutes, and air-dried. Subsequently, a radiation dose of each dot was measured by autoradiography to calculate the strength of the hybridization.

The results are shown in Table 6. In Table 6, a radiation dose for background when the surface active agent sodium N-lauroylsarcosinate) was used was given the scope 1, and other radiation doses are represented by relative values based on this scope. It has been found that when sodium N-lauroylsarcosinate is added in the hybridization reaction, the addition is effective for decreasing the signal of the background by the non-specific adsorption to the filter, and the strength of hybridization increases, which results in improving the sensitivity of the hybridization.

TABLE 6

| Oligonucleotide | | Nucleotide Sequence | Surface active agent | Radiation dose (relative value) |
|---|---|---|---|---|
| 16 | SEQ ID NO: 16 Control 1 | 5'-XCCTTTTCC-3' | No | 1.5 |
| 16 | SEQ ID NO: 16 Example 1 | 5'-XCCTTTTCC-3' | Yes | 2.2 |
| 24 | SEQ ID NO: 24 Control 2 | 5'-XIIIICCTTTTCCIIII-3' | No | 1.8 |
| 24 | SEQ ID NO: 24 Example 2 | 5'-XIIIICCTTTTCCIIII-3' | Yes | 3.0 |
| Background 1 (for Controls 1 and 2) | | | No | 1.6 |
| Background 2 (for Examples 1 and 2) | | | Yes | 1.0 |

SEQUENCE LISTING ( 1 ) GENERAL INFORMATION:

( i i i ) NUMBER OF SEQUENCES:35

( 2 ) INFORMATION FOR SEQ ID NO:1:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:1:

C C C C T T T T        8

( 2 ) INFORMATION FOR SEQ ID NO:2:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:2:

T T C C C C T T        8

( 2 ) INFORMATION FOR SEQ ID NO:3:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:3:

C C T T T T C C        8

( 2 ) INFORMATION FOR SEQ ID NO:4:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:4:

C T C T C T C T        8

( 2 ) INFORMATION FOR SEQ ID NO:5:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:

(B) LOCATION:
                (C) IDENTIFICATION METHOD:
                (D) OTHER INFORMATION: N represents deoxyinosine (xi) SEQUENCE DESCRIPTION: SEQ ID NO:5:

NNNNCCCCTT TT 12

(2) INFORMATION FOR SEQ ID NO:6:

(i) SEQUENCE CHARACTERISTICS:
                (A) LENGTH: 12
                (B) TYPE: nucleic acid
                (C) STRANDEDNESS: single
                (D) TOPOLOGY: linear (ii) MOLECULE TYPE: other..synthetic oligonucleotide (ix) FEATURE:
                (A) NAME/KEY:
                (B) LOCATION:
                (C) IDENTIFICATION METHOD:
                (D) OTHER INFORMATION: N represents deoxyinosine (xi) SEQUENCE DESCRIPTION: SEQ ID NO:6:

NNNNTTCCCC TT 12

(2) INFORMATION FOR SEQ ID NO:7:

(i) SEQUENCE CHARACTERISTICS:
                (A) LENGTH: 12
                (B) TYPE: nucleic acid
                (C) STRANDEDNESS: single
                (D) TOPOLOGY: linear (ii) MOLECULE TYPE: other..synthetic oligonucleotide (ix) FEATURE:
                (A) NAME/KEY:
                (B) LOCATION:
                (C) IDENTIFICATION METHOD:
                (D) OTHER INFORMATION: N represents deoxyinosine (xi) SEQUENCE DESCRIPTION: SEQ ID NO:7:

NNNNCCTTTT CC 12

(2) INFORMATION FOR SEQ ID NO:8:

(i) SEQUENCE CHARACTERISTICS:
                (A) LENGTH: 12
                (B) TYPE: nucleic acid
                (C) STRANDEDNESS: single
                (D) TOPOLOGY: linear (ii) MOLECULE TYPE: other..synthetic oligonucleotide (ix) FEATURE:
                (A) NAME/KEY:
                (B) LOCATION:
                (C) IDENTIFICATION METHOD:
                (D) OTHER INFORMATION: N represents deoxyinosine (xi) SEQUENCE DESCRIPTION: SEQ ID NO:8:

NNNNCTCTCT CT 12

(2) INFORMATION FOR SEQ ID NO:9:

(i) SEQUENCE CHARACTERISTICS:
                (A) LENGTH: 21
                (B) TYPE: nucleic acid
                (C) STRANDEDNESS: single
                (D) TOPOLOGY: linear ( i i ) MOLECULE TYPE: other..synthetic oligonucleotide ( x i ) SEQUENCE DESCRIPTION: SEQ ID NO:9:

AGGAAAAGGG GAAGAGAGAG A                    21

( 2 ) INFORMATION FOR SEQ ID NO:10:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:10:

CCTTTTCC                    8

( 2 ) INFORMATION FOR SEQ ID NO:11:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents deoxyinosine ( x i ) SEQUENCE DESCRIPTION: SEQ ID NO:11:

NNNNCCTTTT CC                    12

( 2 ) INFORMATION FOR SEQ ID NO:12:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents deoxyinosine ( x i ) SEQUENCE DESCRIPTION: SEQ ID NO:12:

NNNNCCTTTT CCNNNN                    16

( 2 ) INFORMATION FOR SEQ ID NO:13:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents deoxyinosine ( x i ) SEQUENCE DESCRIPTION: SEQ ID NO:13:

NNNNNNNNCC TTTTCC    16

( 2 ) INFORMATION FOR SEQ ID NO:14:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents deoxyinosine ( x i ) SEQUENCE DESCRIPTION: SEQ ID NO:14:

NNNNNNNNCC TTTTCCNNNN NNNN    24

( 2 ) INFORMATION FOR SEQ ID NO:15:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:15:

AGAGAGAGAG GAAAAGGAGA GAGAGA    26

( 2 ) INFORMATION FOR SEQ ID NO:16:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:16:

CCTTTTCC    08

( 2 ) INFORMATION FOR SEQ ID NO:17:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:17:

TCTTTTCC    8

( 2 ) INFORMATION FOR SEQ ID NO:18:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:18:

CCTGTTCC                                                                                                       8

( 2 ) INFORMATION FOR SEQ ID NO:19:

( i ) SEQUENCE CHARACTERISTICS:
        ( A ) LENGTH: 8
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:19:

CCTTTTCT                                                                                                       8

( 2 ) INFORMATION FOR SEQ ID NO:20:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:20:

NNNNCCTTTT CC                                                                                                  12

( 2 ) INFORMATION FOR SEQ ID NO:21:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:21:

NNNNTCTTTT CC                                                                                                  12

( 2 ) INFORMATION FOR SEQ ID NO:22:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:22:

NNNNCCTGTT CC                                                    12

( 2 ) INFORMATION FOR SEQ ID NO:23:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:23:

NNNNCCTTTT CT                                                    12

( 2 ) INFORMATION FOR SEQ ID NO:24:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:24:

NNNNCCTTTT CCNNNN                                                16

( 2 ) INFORMATION FOR SEQ ID NO:25:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:25:

NNNNTCTTTT CCNNNN                                                16

( 2 ) INFORMATION FOR SEQ ID NO:26:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:

( C ) IDENTIFICATION METHOD:
( D ) OTHER INFORMATION: N represents inosine ( x i ) SEQUENCE DESCRIPTION: SEQ ID NO:26:

NNNNCCTGTT CCNNNN                                                                      16

( 2 ) INFORMATION FOR SEQ ID NO:27:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:27:

NNNNCCTTTT CTNNNN                                                                      16

( 2 ) INFORMATION FOR SEQ ID NO:28:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:28:

NNNNNNNCC TTTTCC                                                                       16

( 2 ) INFORMATION FOR SEQ ID NO:29:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
        ( A ) NAME/KEY:
        ( B ) LOCATION:
        ( C ) IDENTIFICATION METHOD:
        ( D ) OTHER INFORMATION: N represents inosine ( x i ) SEQUENCE DESCRIPTION: SEQ ID NO:29:

NNNNNNNTC TTTTCC                                                                       16

( 2 ) INFORMATION FOR SEQ ID NO:30:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: other..synthetic oligonucleotide ( i x ) FEATURE:
    ( A ) NAME/KEY:
    ( B ) LOCATION:
    ( C ) IDENTIFICATION METHOD:
    ( D ) OTHER INFORMATION: N represents inosine ( x i ) SEQUENCE DESCRIPTION: SEQ ID NO:30:

NNNNNNNNCC TGTTCC     16

( 2 ) INFORMATION FOR SEQ ID NO:31:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( i i ) MOLECULE TYPE: other..synthetic oligonucleotide ( i x ) FEATURE:
    ( A ) NAME/KEY:
    ( B ) LOCATION:
    ( C ) IDENTIFICATION METHOD:
    ( D ) OTHER INFORMATION: N represents inosine ( x i ) SEQUENCE DESCRIPTION: SEQ ID NO:31:

NNNNNNNNCC TTTTCT     16

( 2 ) INFORMATION FOR SEQ ID NO:32:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: other..synthetic oligonucleotide ( i x ) FEATURE:
    ( A ) NAME/KEY:
    ( B ) LOCATION:
    ( C ) IDENTIFICATION METHOD:
    ( D ) OTHER INFORMATION: N represents inosine ( x i ) SEQUENCE DESCRIPTION: SEQ ID NO:32:

NNNNNNNNCC TTTTCCNNNN NNNN     24

( 2 ) INFORMATION FOR SEQ ID NO:33:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: other..synthetic oligonucleotide ( i x ) FEATURE:
    ( A ) NAME/KEY:
    ( B ) LOCATION:
    ( C ) IDENTIFICATION METHOD:
    ( D ) OTHER INFORMATION: N represents inosine ( x i ) SEQUENCE DESCRIPTION: SEQ ID NO:33:

NNNNNNNNTC TTTTCCNNNN NNNN     24

( 2 ) INFORMATION FOR SEQ ID NO:34:

( i ) SEQUENCE CHARACTERISTICS:
    ( A ) LENGTH: 24
    ( B ) TYPE: nucleic acid

```
            ( C ) STRANDEDNESS: single
            ( D ) TOPOLOGY: linear ( i i ) MOLECULE TYPE: other..synthetic oligonucleotide ( i x ) FEATURE:
            ( A ) NAME/KEY:
            ( B ) LOCATION:
            ( C ) IDENTIFICATION METHOD:
            ( D ) OTHER INFORMATION: N represents inosine ( x i ) SEQUENCE DESCRIPTION: SEQ ID NO:34:

NNNNNNNNCC TGTTCCNNNN NNNN                                              2 4

( 2 ) INFORMATION FOR SEQ ID NO:35:

( i ) SEQUENCE CHARACTERISTICS:
            ( A ) LENGTH: 24
            ( B ) TYPE: nucleic acid
            ( C ) STRANDEDNESS: single
            ( D ) TOPOLOGY: linear ( i i ) MOLECULE TYPE: other..synthetic oligonucleotide ( i x ) FEATURE:
            ( A ) NAME/KEY:
            ( B ) LOCATION:
            ( C ) IDENTIFICATION METHOD:
            ( D ) OTHER INFORMATION: N represents inosine ( x i ) SEQUENCE DESCRIPTION: SEQ ID NO:35:

NNNNNNNNCC TTTCTNNNN NNNN                                               2 4
```

What is claimed is:

1. An oligonucleotide which is used for an analysis of a base sequence of a sample nucleic acid by hybridization, consisting of a specific region and one or two non-specific regions which are covalently linked to at least one of the two termini of the specific region, wherein the specific region has a specific base sequence for analyzing complementarity to a target sequence of a sample nucleic acid with which the oligonucleotide is to be hybridized, the non-specific region or each of the non-specific regions consisting of two or more nucleotides, each of the nucleotides having a base other than an ordinary base selected from the group consisting of adenine, guanine, cytosine, thymine and uracil, which base is capable of forming a base pair with each of the ordinary bases.

2. The oligonucleotide of claim 1, wherein a base-pairing energy between the ordinary base and the base other than the ordinary base is weaker than a base-pairing energy between the ordinary bases.

3. The oligonucleotide of claim 2 wherein the other base is hypoxanthine.

4. The oligonucleotide of claim 1 which is oligodeoxyribonucleotide.

5. The oligonucleotide of claim 1 wherein said oligonucleotide comprises one non-specific region and the non-specific region is bound to the 5' terminus of the specific region.

6. The oligonucleotide of claim 1 wherein said oligonucleotide comprises two non-specific regions and the non-specific regions are bound to both the 5' terminus and the 3' terminus of the specific region.

7. The oligonucleotide of claim 1 wherein the length of the non-specific region or each of the non-specific regions comprises from 2 to 20 bases.

8. The oligonucleotide of claim 7 wherein the length of the specific region comprises from 6 to 50 bases.

9. The oligonucleotide of claim 8, wherein the length of the specific region is the same or more than that of the non-specific region or each of the non-specific regions.

10. The oligonucleotide of any one of claims 1 to 6, 8 and 9 which is immobilized on an insoluble carrier.

11. The oligonucleotide of claim 10, which is immobilized on the insoluble carrier at the 5' terminus of said oligonucleotide.

12. A method for analyzing a base sequence of a nucleic acid, which comprises a step of hybridizing an oligonucleotide consisting of a specific region and one or two non-specific regions which are covalently linked to at least one of the two termini of the specific region, wherein the specific region has a specific base sequence for analyzing complementarity to a target sequence of a sample nucleic acid with which the oligonucleotide is to be hybridized, the non-specific region or each of the non-specific regions consisting of one or more nucleotides, each of the nucleotides having a base other than an ordinary base selected from the group consisting of adenine, guanine, cytosine, thymine and uracil, which is capable of forming a base pair with each of the ordinary bases, with a sample nucleic acid, and a step of discriminating the presence or absence of a target sequence complementary to the base sequence of the specific region of said oligonucleotide in the sample nucleic acid by the strength of the hybridization or by the presence or absence of the hybridization.

* * * * *

UNITED STATES PATENT AND TRADEMARK OFFICE
CERTIFICATE OF CORRECTION

PATENT NO. : 5,738,993
DATED : April 14, 1998
INVENTOR(S) : Nobutake FUGONO et al.

It is certified that error appears in the above-identified patent and that said Letters Patent is hereby corrected as shown below:

On the title page:

<u>IN THE ASSIGNEE</u>:

In Section [73], Assignee, before "Japan" insert --Tokyo--.

Signed and Sealed this

Eighteenth Day of August, 1998

Attest:

BRUCE LEHMAN

Attesting Officer  Commissioner of Patents and Trademarks